United States Patent [19]

Ng et al.

[11] Patent Number: 5,336,505
[45] Date of Patent: Aug. 9, 1994

[54] BIOERODIBLE POLYMERS USEFUL FOR THE CONTROLLED RELEASE OF THERAPEUTIC AGENTS

[75] Inventors: Steve Y. W. Ng, San Francisco; Jorge Heller, Woodside, both of Calif.

[73] Assignee: Pharmaceutical Delivery Systems, Menlo Park, Calif.

[21] Appl. No.: 725,319

[22] Filed: Jul. 8, 1991

Related U.S. Application Data

[63] Continuation-in-part of Ser. No. 568,433, Aug. 16, 1990, abandoned, which is a continuation-in-part of Ser. No. 556,645, Jul. 20, 1990, abandoned, which is a continuation-in-part of Ser. No. 400,532, Aug. 28, 1989, Pat. No. 5,030,457.

[51] Int. Cl.$^5$ .......................... A61K 9/14; A61F 2/00
[52] U.S. Cl. .................... 424/486; 424/423; 424/457; 528/425
[58] Field of Search ............. 528/425; 424/486, 423, 424/457

[56] References Cited

U.S. PATENT DOCUMENTS

| | | | |
|---|---|---|---|
| 4,066,747 | 1/1978 | Capozza | 424/78 |
| 4,079,038 | 3/1978 | Choi et al. | 528/176 |
| 4,119,579 | 10/1978 | Capozza | 526/270 |
| 4,122,158 | 10/1978 | Schmitt | 424/27 |
| 4,186,185 | 1/1980 | Capozza | 424/19 |
| 4,304,767 | 12/1981 | Heller et al. | 424/78 |
| 4,405,798 | 9/1983 | Hall et al. | 549/363 |
| 4,549,010 | 10/1985 | Sparer et al. | 528/361 |
| 4,814,173 | 3/1989 | Song et al. | 424/444 |
| 5,030,457 | 7/1991 | Ng et al. | 424/486 |

FOREIGN PATENT DOCUMENTS

0208617 1/1987 European Pat. Off. .

OTHER PUBLICATIONS

Burt et al., "Hydrolysis of bicyclic ortho esters in the 2,6,7-trioxabicyclo[2.2.1]heptane series. Confirmation of the absence of strain-relief rate acceleration" *J. Am. Chem. Soc.* (1982) 104:3687–3690.

Heller et al., "Controlled drug release from bioerodible hydrophobic ointments" *Biomaterials* (1990) 11:235–237.

Padías et al., "Synthesis and polymerization of pentaerythritol acrylate and methacrylate and their bicyclic ortho esters" *Macromolecules* (1982) 15(2):217–223.

Padías et al., "Synthesis and polymerization of atom-bridged bicyclic acetyls and orthoesters; a new mechanism" pp. 258–259.

Padías et al., "Synthesis and polymerization of atom-bridged bicyclic acetyls and ortho esters" ACS Symposium Series, American Chemical Society, Washington, D.C., (1985) 286:313–333.

Pulapura et al., "Structure-property relationships for the design of polyiminocarbonates" *Biomaterials* (1990) 11:666–678.

Szyma ski et al., "Novel cationic and anionic water-soluble polyrthoesters" *J. Polymer Sci.* (1983) 21:177–187.

Yokoyama et al., "Polymerization of bicyclic compounds having oxygen atoms" *Adv. Polymer Sci.* (1982) 42:109–138.

Primary Examiner—John Kight, III
Assistant Examiner—T. Mosley
Attorney, Agent, or Firm—Viviana Amzel

[57] ABSTRACT

Bioerodible ortho ester polymers useful for preparing bioerodible pharmaceutical compositions such as implants, ointments, creams, gels and the like are provided. The pharmaceutical compositions of the invention are useful for the controlled release of therapeutic agents, and may be administered for a variety of purposes, such as for the treatment of deep wounds, including burns, and for the treatment of periodontal disease.

31 Claims, 1 Drawing Sheet

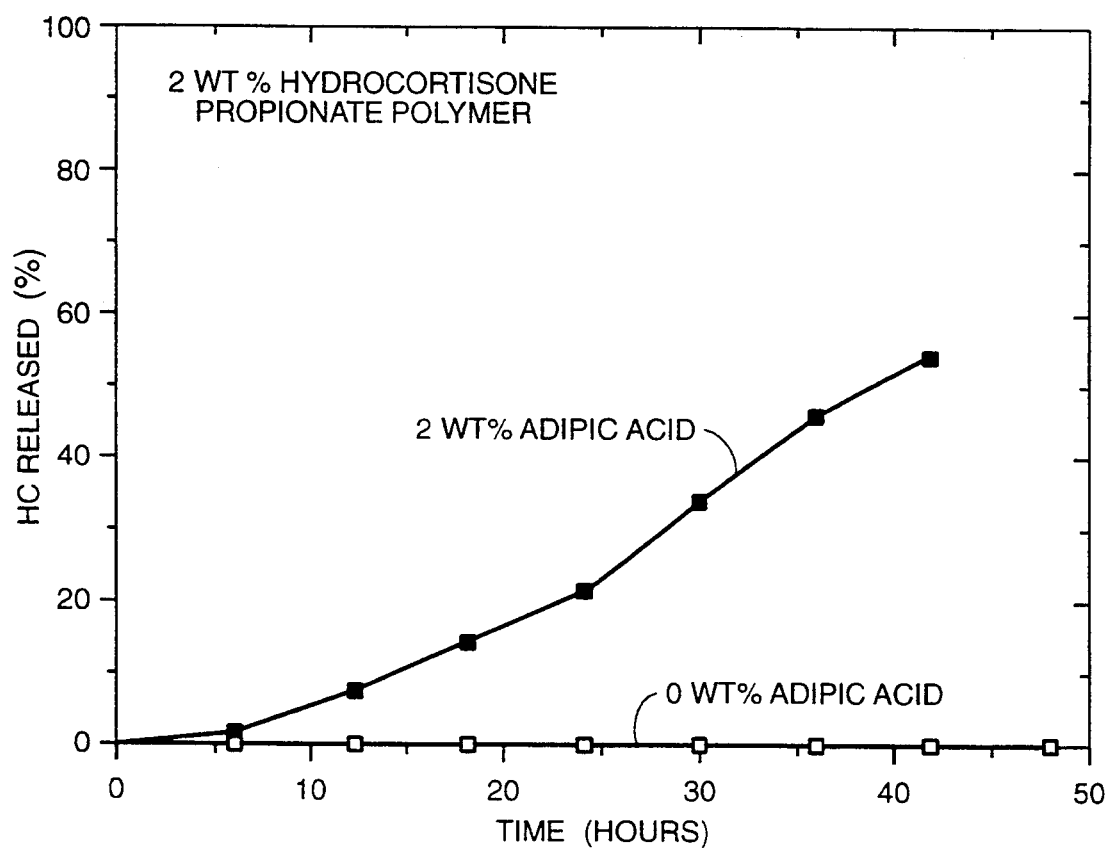
FIG._1

BIOERODIBLE POLYMERS USEFUL FOR THE CONTROLLED RELEASE OF THERAPEUTIC AGENTS

CROSS-REFERENCE TO RELATED APPLICATION

This application is a continuation-in-part of U.S. patent application Ser. No. 07/568,433 filed Aug. 16, 1990, now abandoned, which is a continuation-in-part of U.S. patent application Ser. No. 07/556,645, filed 20 Jul. 1990 and now abandoned, which is a continuation-in-part of U.S. patent application Ser. No. 07/400,532, filed 28 Aug. 1989 and issued as U.S. Pat. No. 5,030,457 on 9 Jul. 1991, the disclosures of which are incorporated by reference herein.

TECHNICAL FIELD

The present invention is in the fields of polymer chemistry and drug delivery, and concerns certain ortho ester polymers and methods for their preparation. These materials are bioerodible polymers, i.e., polymers containing hydrolytically labile linkages which undergo cleavage at physiologic conditions. These bioerodible polymers are useful for the controlled release of therapeutic agents. Thus, the invention relates to drug dosage forms prepared with the novel polymers, including solid implantable drug dosage forms as well as soft forms such as ointments, gels, creams and the like. The invention additionally relates to the use of these bioerodible drug dosage forms in the treatment of disease conditions such as deep wounds, periodontal disease, and the like.

BACKGROUND OF THE INVENTION

Bioerodible polymers used to control the release of therapeutic agents physically dispersed in the polymer matrix have been described in a variety of contexts. One matrix which has been successful is a family of poly(ortho esters). These materials contain the pH-sensitive ortho ester linkage in their polymer backbone. Such polymers are described, for example, in U.S. Pat. No. 4,304,767 to Heller et al. Because the ortho ester linkages within these polymers are relatively stable at neutral pH, and hydrolyze progressively faster with the decreasing pH of the surrounding medium, the rate of erosion of the polymer can be manipulated within a very wide range by incorporating various levels and strengths of acidic excipients into the polymer matrix.

The method of preparing polymers according to the aforementioned patent comprises the addition of polyols to diketene acetals as shown in Scheme 1.

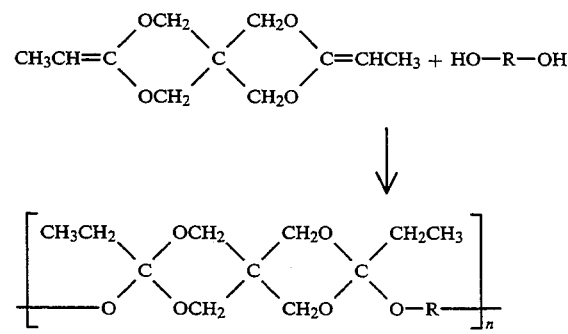

Using this scheme, almost any diketene acetal and any diol can be used, and the synthetic method is thus extremely versatile. Polymers synthesized by this method are, however, not optimal for preparing soft or amorphous drug dosage forms such as bioerodible ointments, creams or gels due to the relatively rigid pentaerythritol segment in the polymer backbone.

There is a need in the art for a bioerodible composition which has a molecular structure of sufficient flexibility to enable its use as a bioerodible matrix in soft dosage forms such as ointments, gels, creams, or the like. An ideal material would enable the topical delivery of an effective dose level of pharmaceutical agent from an ointment or the like at a desired rate for a period of time dictated only by clinical considerations and not by limitations of the ointment, cream or gel formulation. The ability to achieve this is particularly important in cases where excessive and uncontrolled application of a drug can produce serious side effects.

SUMMARY OF THE INVENTION

This invention provides a subset of the family of ortho ester materials broadly taught in U.S. Pat. No. 5,030,457. This subset of ortho ester materials contains a mer unit having the structure

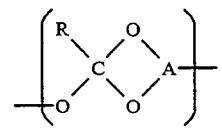

wherein R is alkyl of 1 to 5 carbon atoms and A is selected rom the group consisting of cycloalkylenes of at least 5 carbon atoms, cyclooxyalkylenes of at least 5 carbon atoms, and alkylenes having the structure

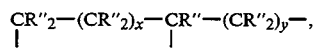

wherein x is 0 or 1, y is greater than or equal to 3, and the R″s are independently selected from the group consisting of hydrogen and lower alkyl.

These materials constitute a subset in that the parent R can be hydrogen or a 1 to 10 carbon alkyl. This subset offers the advantage of providing a wide range of consistent controllable release rates. The release rate varies directly with R group size. When R is $CH_3$, the rate is fast; when R is $—(CH_2)_4CH_3$, it is slow. These materials are rigid or nonrigid materials depending upon the A group and find application in ointments, solid dosage forms, and the like.

The invention also provides ointments and other rigid and nonrigid pharmaceutical drug dosage forms formulated from these preferred ortho esters. These drug dosage forms can include optional addition of carriers and/or diluents and can also include neutral, acid or base materials to act as excipients and, in the case of acid, enhance the rate of ortho ester polymer breakdown or, in the case of base, slow or delay this breakdown.

These ortho ester materials are formed by reacting a monomeric ortho ester having the general formula

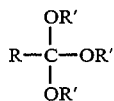

wherein R is an alkyl of 1 to 5 carbon atoms and R' is lower alkyl with a triol having the general formula

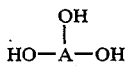

wherein A is selected from alkylenes and cycloalkylenes of at least 5 carbon atoms and oxyalkylenes and cyclooxyalkylenes of at least 5 carbons.

In another aspect of the invention it has been found that the material of U.S. Pat. No. 5,030,457, as a general class, that is, wherein R is hydrogen or an alkyl of 1 to 10 carbon atoms, can be incorporated into solid or semi-rigid drug dosage forms such as solid implants or the like. They can be accompanied, if desired, by carriers or neutral, acidic or basic excipients as already described.

In a related aspect this invention provides another subset of the ortho ester materials taught in the parent patent. This subset of ortho ester materials include a mono- or dialkylene cyclohexylene A unit, denominated A*. These materials are formed by reacting a monomeric ortho ester having the general formula

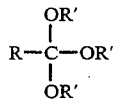

wherein R is hydrogen or alkyl of 1 to 10 carbon atoms and R' is lower alkyl, with a mono- or dialkylenecyclohexylene-based triol having the general formula

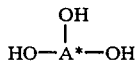

wherein A* is

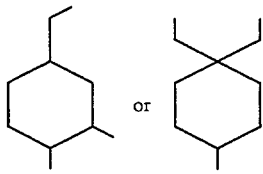

to form a bioerodible ortho ester polymer comprising mer units of the structure

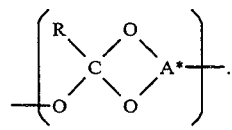

The materials which include the A* groups are characterized by being among the more rigid of this family of ortho ester polymers. Drug dosage forms made from these polymers tend to be more solid and can be most advantageously configured as degradable solid implants and the like. These drug-containing dosage forms with or without carriers and acidic, basic or neutral excipients constitute additional aspects of the invention as does the above-described preparation method.

Thus, bioerodible pharmaceutical compositions are provided based on these ortho ester polymers. These compositions are either in solid implantable form or in a soft dosage form and contain one or more of the aforementioned bioerodible ortho ester polymers along with an effective amount of a selected therapeutic agent.

In another aspect, the invention relates to a method for the prolonged treatment of disease states in man and animals such as treating burns, deep wounds, and the like. This method comprises administering to such a patient a pharmaceutical composition of the invention so as to achieve controlled bioerosion of the ortho ester polymer and thus give rise to gradual exposure to and controlled delivery of the therapeutic agent.

BRIEF DESCRIPTION OF THE DRAWINGS

FIG. 1 is a graph illustrating the effect of an acidic excipient on the rate of bioerosion of the ortho-ester-based compositions of this invention.

DETAILED DESCRIPTION OF THE PREFERRED EMBODIMENT OF THE INVENTION

A. Definitions

The term "mer" is used to mean the structurally recurring units or monomer units of the ortho ester polymers provided by the present invention. The mer units of any given polymer may be the same or different; when different, they may be arranged in block or random fashion. When all the mer units of a polymer are the same, the polymer is called a homopolymer. When there are 2 or more mer units in a polymer, the polymer is called a copolymer. The present invention involves both homopolymers and copolymers.

The term "bioerodible" as used herein to describe the polymers of the present invention is synonymous with the term of art "biodegradable." These terms denote the property of a body of solid gel polymer to undergo degradation, erosion and solubilization as a result of hydrolysis of labile linkages at the physiologic conditions of use.

The terms "therapeutic agent" or "drug" are used interchangeably to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine.

The term "effective amount" as used herein intends that quantity of a therapeutic agent that, when administered to a patient, is required to provide the desired or intended beneficial effect without intolerable side effects, such as toxicity. When used in the context of controlled delivery or prolonged delivery of drug, the term can include a temporal aspect—noting that the rate of administration gives the desired effect without intolerable side effects.

The term "soft dosage form" as used herein is intended to mean a bioerodible ointment, gel, cream or the like, typically intended for topical administration of a drug.

The term "implantable" drug dosage form as used herein is intended to mean a drug-bearing polymeric body designed to be implanted subcutaneously or in a body cavity so as to give rise to sustained release of the contained drug.

The term "lower alkyl" is intended to mean linear, branched or cyclic alkyl moieties having 1 to 6, and more typically 1-5 carbon atoms, inclusive.

The terms "alkylene" and "cycloalkylene" have their usual meaning defining aliphatic linking groups, noncyclic in the case of "alkylene", and including a nonaromatic ring structure in the case of "cycloalkylene", preferably aliphatic hydrocarbon groups which serve as a bridge between 2 or more other groups. A "cycloalkylene" group can have noncyclic groups extending from its ring as alkyl substituents or as alkylene linking groups.

The term "oxyalkylene" defines an aliphatic linking group containing 1 or more ether oxygens and providing 2 or more carbons as bridge points to other groups. Oxyalkylene groups can be linear, branched or cyclic.

An ideal material for a bioerodible matrix in soft dosage forms would enable the tropical delivery of an effective dose level of pharmaceutical agent form an ointment or the like at a desired rate for a period of time dictated only by clinical considerations and not by limitations of the ointment, cream or gel formulation. The ability to achieve this is particularly important in cases where excessive and uncontrolled application of a drug can produce series side effects.

The resent invention is addressed to these considerations, and provides bioerodible compositions which may be prepared in either solid implantable forms or in soft dosage forms such as ointments or the like as noted above. In these bioerodible drug dosage forms, the release rate of the drug to be delivered as well as the desired time period for drug delivery can be carefully controlled. In addition, the drug dosage forms of the invention are comprised of materials which bioerode to small, water-soluble molecules that leave no residues in the tissue of a patient undergoing treatment. This opens the door for improved treatment of burns, wounds, especially deep wounds, and like applications by the controlled delivery of drugs over prolonged periods of time.

The present invention constitutes an improvement over the invention claimed in U.S. Pat. No. 5,030,457. That patent describes a family of bioerodible orthoester polymers, their use in pharmaceutical compositions and a method for their preparation. The method involves reacting a monomeric orthoester of the chemical formula

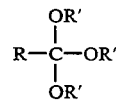

wherein R is hydrogen or (C$_1$-C$_{10}$)alkyl, and R' is (C$_1$-C$_6$) lower alkyl, with a triol having the chemical formula

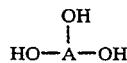

wherein A is alkylene or cycloalkylene of at least 5 carbon atoms, or an oxyalkylene or cyclooxyalkylene of at least 5 carbons and having its oxygen as an ether linkage, e.g., within a saccharide structure. This reaction forms an orthoester polymer containing a mer unit having the chemical formula

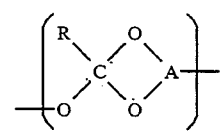

wherein the A and R units are as just described.

The orthoester materials of that patent were typically flexible, non-rigid materials, which lent themselves to ointments and salve-like formulations. The present invention provides in some embodiments improved non-rigid materials, but in other embodiments makes available more rigid materials which find application in erodible solid implants and the like.

It is a primary object of the present invention to address the aforementioned needs in the art, and to improve upon and extend the invention claimed in bioerodible compositions and drug dosage forms for the controlled release of therapeutic agents.

B. Synthetic Method

Parent application Ser. No. 07/400,532, incorporated by reference above (U.S. Pat. No. 5,030,457 that issued 9 Jul. 1991), describes the preferred method of synthesizing the bioerodible ortho ester polymers of the present invention. For the sake of completeness, this method will be reproduced herein. As described in the parent application, the synthesis is a simple, straightforward reaction which may be accomplished in one stp in a single reaction vessel. The synthesis involves the reaction of a monomeric ortho ester having the general formula

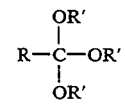

wherein R is a hydrogen or an alkyl of 1 to 10 carbon atoms and each of the R's is independently selected from lower alkyls, with a triol having the general formula

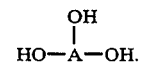

In this triol, A includes A* and is an alkylene or a cycloalkylene moiety of 5 carbon atoms or more, or is an oxyalkylene or cyclooxyalkylene. If cycloalkylene or a cyclooxyalkylene, A will preferably contain 1 to 3, more preferably 1 or 2, rings. The reaction is carried out to form an ortho ester polymer which comprises mer units of the structure (I)

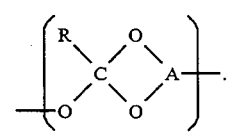

In preferred embodiments, the R moiety of the monomeric ortho ester reactant is lower alkyl that is a 1 to 5 carbon alkyl, and the R' moieties are the same alkyl, either methyl or ethyl. In preferred embodiments, the triol reactant includes an A moiety which is either alkylene or cycloalkylene or oxyalkylene of 5 carbon atoms or more, preferably 5 to 20 carbon atoms, and more preferably 5 to 10 carbon atoms. It is preferred that 2 of the hydroxyl groups of the triol be separated by either 2 or 3 carbon atoms (e.g., so that x in the below structures is 0 or 1, respectively), to enable ring formation during polymerization, while the third hydroxyl group is preferably separated from the closer of the first 2 hydroxyl groups by 3 carbon atoms or more, (e.g., so that in the below structures y is greater than or equal to 2). This spacing of the third hydroxyl unit will prevent interference with the ring-forming reaction. Thus, in one group of preferred triols, A is a linear alkylene moiety, i.e., having the structure

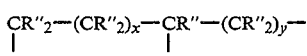

so that the triol has the structure

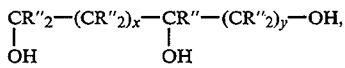

in which the various R" groups are independently selected from the group consisting of hydrogen and lower alkyls, x is 0 or 1, and y is greater than or equal to 2. If A is cycloalkylene, the ring structure preferably is such as to give this preferred hydroxyl spacing and facilitate ring closure.

Examples of cycloalkylene A moieties include the A* mono- and dialkylenecyclohexylenes which are found in the triols

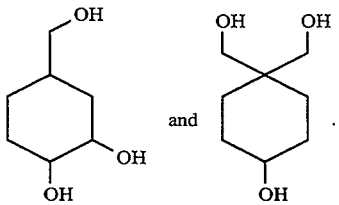

If oxyalkylene, A may be a cyclic sugar residue in which 2 of the triol hydroxyl moieties are α, β-cis so as to facilitate ring formation, while the other, third hydroxyl moiety is trans to the first 2 hydroxyl groups and separated therefrom by 3 or more carbon atoms, typically located in the 5'-position of a pentafuranose (cyclooxyalkylene) A ring as in the structure:

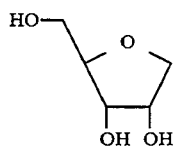

Compounds containing analogous substituted pentafuranose rings are within the purview of the present invention as well.

The synthesis reaction of the ortho ester monomer and triol is carried out either neat or in an aprotic solvent such as tetrahydrofuran (THF), cyclohexane, ethylene glycol dimethyl ether (glyme), diglyme, cymene, cumene, chlorinated hydrocarbons, or the like. More typically, solvent is present. Typical concentrations of the two reactants can range from essentially 100% (neat) down through about 10% by weight or lower, when solvent is used. In either case, care must be taken to maintain anhydrous conditions. The reaction can be carried out at reflux and thus, depending upon the solvent, at temperatures in the range of 50°–150° C., preferably 50°–90° C. The approximate molar ratio of reactants set at about 1:1 if it is desired to maximize the molecular weight of the polymer, but can be varied if a lower molecular weight polymer is desired (e.g., to make a less viscous ointment). It is typically preferred to carry out the reaction in the presence of an acid catalyst, although in cases where the reactants are acidic, a catalyst is unnecessary. Examples of suitable acid catalysts include p-toluenesulfonic acid and methanesulfonic acid. The amount of acid catalyst can range from 0% (based on its optional presence) to about 1% molar (based on the amount of triol present).

C. The Bioerodible Polymers

The ortho ester polymers useful in the drug dosage forms provided herein preferably contain met units represented by Formula (I) wherein

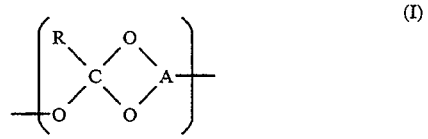

R is hydrogen or an alkyl of 1 to 10 carbon atoms, preferably a lower alkyl of 1 to 5 carbon atoms; and A is a cycloalkylene of at least 5 carbon atoms, a cyclooxyalkylene of at least 5 carbon atoms (as in the pentafuranose ring and other cyclooxyalkylene structures illustrated above), or a linear or branched alkylene moiety of at least 5 carbon atoms given by the structure

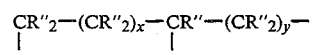

this latter structure, the R" moieties are independently selected from the group consisting of hydrogen and the lower alkyls, x is 0 or 1, and y is an integer greater than or equal to 3.

Typically, although not necessarily, the polymers of the invention have molecular weights ranging from several (2–3) thousand to 10,000–15,000, but can have molecular weights as low as 500 or as high as 50,000 or more. The number of met units in the polymer, correspondingly, will be between about 5 and 1000, more typically between about 5 and 500, most typically between about 5 and 150.

These polymers have the desirable properties of being able to undergo bioerosion and of being capable of having their properties tailored to be less rigid and more flexible and conforming than prior ortho ester polymers, if desired, or, in the case of the cyclohexylene A*-containing material, somewhat rigid.

C. Pharmaceutical Compositions

The pharmaceutical compositions of this invention comprise a selected therapeutic agent or number of agents admixed with, i.e., dispersed in one or more of, the bioerodible ortho ester polymers as described in the preceding section. While the preferred pharmaceutical compositions of the invention include solid implantable drug dosage forms and soft dosage forms such as bioerodible ointments, gels and creams, it is intended that other drug dosage forms and other modes of administration (e.g., transdermal, transmucosal, intraocular, etc.) be within the scope of the invention as well.

The bioerodible ointments, gels and creams of the invention will include an ointment, gel or cream base comprising one or more of the nonrigid bioerodible ortho ester polymers described herein and a selected therapeutic agent. The nonrigid ortho ester itself can serve as a carrier or gel or cream base for these soft dosage forms. If desired, other known ointment base components as described in Remington's Pharmaceutical Sciences, 17th Edition, Mack Publishing Company, Easton, Pa., 1985, can be incorporated. The therapeutic agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate, and the like. The solid implantable formulation to be administered will contain a quantity of active compound or compounds in an amount effective to alleviate the symptoms of the subject being treated.

The amount of active agent will be dependent upon the particular drug employed and condition being treated. Typically the amount of drug represents about 0.001% to about 70%, more typically about 0.001% to about 50%, most typically about 0.001% to about 20% by weight of the total composition being common.

The quantity and type of ortho ester polymer incorporated into the implant, ointment, gel, cream, etc., is variable. For a more viscous composition, a higher molecular weight polymer is used. If a less viscous composition is desired, a lower molecular weight polymer can be employed, i.e., one which is prepared with other than a 1:1 reactant ratio. The product may be based on only one polymer or it may comprise a mixture of polymers. Typically the product should include from at least about 25% to about 100% of its carrier (non-drug) as the present polymers.

While not essential for topical or transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N,N-dimethylacetemide (DMA), desylmethylsulfoxide ($C_{10}MSO$), ethanol, eucalyptol, lecithin, and the 1-N-dodecylcyclazacycloheptan-2-ones (available under the trademark Azone® from the Nelson Research and Development Company, Irvine, Calif.).

It is additionally preferred to incorporate an acidic or basic excipient into the bioerodible dosage form in order to control the rate of polymer bioerosion. The ortho ester linkages of the bioerodible polymers are relatively stable at basic or neutral pH and are hydrolized at progressively increasing rates as the pH of the medium surrounding the polymer decreases. Thus, hydrolytic lability and the rate of erosion and drug release can be increased by incorporation of one or more acidic components. Preferred acidic excipients are aliphatic acids, typically present at 0–10 wt %, more preferably 1–5 wt %, of the bioerodible composition. Solid but water soluble aliphatic acids are generally favored. Examples of acidic excipients useful in conjunction with the present invention include adipic, citric, suberic, maleic and itaconic acids. Basic excipients, e.g., sodium carbonate, potassium carbonate, potassium bicarbonate, magnesium hydroxide, calcium lactate or the like, may also be used in amounts of 0–10% by weight to slow the rate of release. In the case of basic excipients, they can slow the release rate to essentially zero. If the basic material is leachable by fluids in the environment of use, and is eventually removed. This can have the effect of delaying the onset of delivery until the base is removed and the pH lowers to a level at which the ortho esters are broken down.

The variety of different therapeutic agents which can be used in conjunction with the bioerodible compositions of the invention is vast. In general, therapeutic agents which may be administered via the pharmaceutical compositions of the invention include, without limitation: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

In particularly preferred embodiments the therapeutic agents for administration in conjunction with the bioerodible polymers of the invention are antibacterial agents for the treatment of deep wounds, antibiotics (e.g., tetracycline or the like) for periodontal treatment or subcutaneous/subgingival abscesses, antiinflammatory agents (e.g., meclofenamate sodium, oxyphenbutazone, indomethacin, mefenamic acid, ibuprofen, and naproxen, etc.), antibiotics and adrenal corticosteroids for use in intraarticular injection or implantation, intraocular/orbital adrenal corticosteroids, antiviral agents or antibiotics, and antihypertensive agents (e.g., hydralazine, minoxidil or the like). Other preferred drugs for use with the presently disclosed polymers include proteinaceous drugs such as epidermal growth factors or growth hormones.

The present invention also encompasses veterinary applications of the presently disclosed polymers, pharmaceutical compositions, and methods of treatment.

D. Administration and Use

Depending on dosage form, the pharmaceutical compositions of the preceding section may be administered in different ways, i.e., topically, parenterally, or the like. Preferred dosage forms are solid implants or soft dosage forms which can be applied directly to the afflicted tissue for the delivery of drug. The ortho ester polymer, upon contact with body fluids including perspiration, saliva, or the like (depending upon the mode of administration), undergoes gradual bioerosion with concomitant gradual exposure of the dispersed drug to the afflicted tissue. This can result in prolonged delivery (over, say, 1 to 10,000 hours, preferably 2 to 1000 hours) of effective amounts (say, 0.0001 mg/kg/hour to 10 mg/kg/hour) of the drug. Application can be repeated as necessary depending on the subject being treated, the severity of the affliction, the judgment of the prescribing physician, and the like. Topical application can be enhanced by occlusion, i.e., placing a barrier over the area treated so as to enhance absorption into the skin. Topical administration or implantation is preferred for wound healing and in the treatment of periodontal disease.

Parenteral administration of a bioerodible composition of the invention can be effected by either subcutaneous or intramuscular injection. The bioerodible ointment, gel or cream may be injected as is or in combination with one or more auxiliary components as described above. Parenteral delivery is preferred for administration of proteinaceous drugs such as growth factors, growth hormone, or the like.

Intraocular, transdermal or transmucosal administration of bioerodible compositions of the invention can also be carried out according to conventional means.

EXAMPLES

The examples presented below are provided as a further guide to the practitioner of ordinary skill in the art, and are not to be construed as limiting the invention in any way.

EXAMPLE 1

Under anhydrous conditions, 48,669 g (0.30 moles) of triethylorthoacetate, 40.25 g (0.30 moles) of 1,2,6-hexanetriol and 20 mg of p-toluenesulfonic acid were weighed into a 500 ml round bottom flask equipped with a magnetic stirring bar. To the flask was added 300 ml cyclohexane and the flask was adapted to a 60 cm spinning band column. The reaction flask was heated at 100° C. with vigorous stirring and the distillate, which included an azeotrope of-by-product and cyclohexane ethanol, was removed rapidly at 65° C. while a strictly anhydrous condition was maintained. As the boiling point started to climb beyond 65° C., the distillation rate was reduced to 1/20 (distillation/reflux ratio) until the boiling point reached 81° C. Then the column was set at that total reflux. After heating for an additional 4 hours, the solution was cooled to room temperature. Five drops of triethylamine were added and solvent was removed by evaporation. The product was a viscous liquid having a weight average molecular weight (MW) of 29,000 as determined by GPC.

EXAMPLE 2

Following the procedure as described in Example 1, 52.878 g (0.30 mole) of triethylorthopropionate was reacted with 40.25 g (0.30 mole) of 1,2,6-hexanetriol. The by-product ethanol was removed by azeotropic distillation with cyclohexane to yield a polymer having a MW of 19,300.

EXAMPLE 3

Following the procedure as presented in Example 1, 14.82 g (0.10 mole) of trimethylorthobutyrate was reacted with 13.42 g (0.10 mole). The by-product methanol was removed by azeotropic distillation with cyclohexane from 54° C. to 81° C. to yield a polymer having a MW of 27,600.

EXAMPLE 4

Following the procedure as presented in Example 1, 16.223 g (0.10 mole) of triethylorthoacetate was reacted with 12,015 g (0.10 mole) of 1,2,5-pentanetriol to yield a polymer having a MW of 25,000.

EXAMPLE 5

Following the procedure as described in Example 1, 3.82 g (31.74 Moles) of trimethyl orthoacetate was reacted with 4.64 g (31.74 mmoles) of cis-3,4-dihydroxycyclohexanemethanol previously prepared by introducing two OHs into the 3 and 4 positions of cyclohexa-3-enemethanol with an $OsO_4$ catalyst. The byproduct methanol was removed by azeotropic distillation with cyclohexane. After evaporation of the cyclohexane, the polymer was redissolved in tetrahydrofuran and precipitated into a large excess of methanol containing a small amount of triethylamine stabilizer. The solid polymer, isolated by filtration, had a molecular weight ($M_W$) of 25,000.

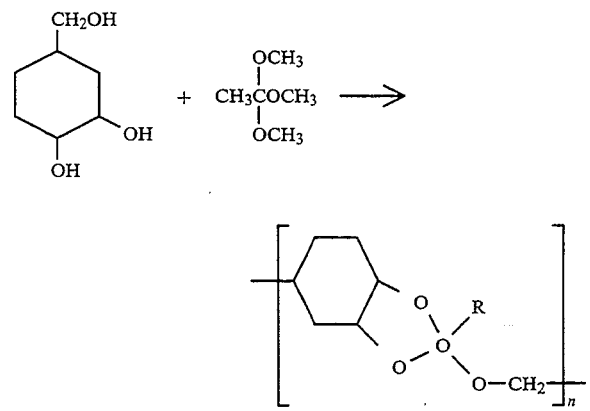

The monomer was prepared as follows:

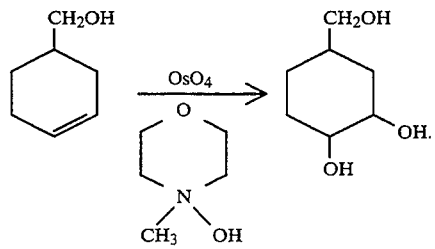

EXAMPLE 6

A bioerodible ointment was prepared with 2 wt % hydrocortisone physically dispersed in a soft, bioerodible ortho ester polymer having the structure

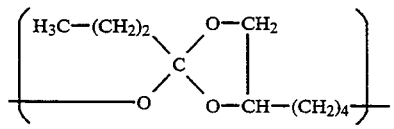

synthesized using the methods described in the preceding examples. To demonstrate bioerodibility, a body of this ointment was exposed to a slow (9 mm/min) flow of buffer solution, pH 7.4. Fractions were collected and the appearance of the drug in the collected buffer was analyzed by HPLC. Because hydrolysis of ortho ester linkages at pH 7.4 is very slow, no hydrocortisone was released in the absence of an incorporated acidic excipient. Upon incorporation of 2 wt % of adipic acid into the bioerodible ointment, bioerosion took place and hydrocortisone was released. Results are summarized graphically in FIG. 1. The rate of hydrocortisone release can thus be controlled by the amount of the incorporated acidic excipient or the use of materials having varying acidity.

EXAMPLE 7

A bioerodible, 20 mm×2 mm cylindrical implant was fabricated by first dissolving the polymer of Example 5 in tetrahydrofuran and then adding to the viscous polymer solution 10 wt % (based on polymer weight) of the anticancer agent 5-fluorouracil. After solvent evaporation, devices were fabricated by transfer molding. To demonstrate bioerodibility, the cylindrical devices were exposed to a slow (9 cc/min) flow of buffer solution, pH 7.4 at 37° C. Fractions were collected, and the appearance of 5-fluorouracil in the collected buffer was analyzed by HPLC. Because hydrolysis of the polymer at pH 7.4 is very slow, no drug was released in the absence of an acidic excipient. Upon incorporation of 1 wt % suberic acid, bioerosion took place and 5-fluorouracil was released. The rate of drug release can thus be controlled by the amount and acidity of the incorporated acidic excipient.

What is claimed is:

1. A polymer comprising repeating mer units of the structure

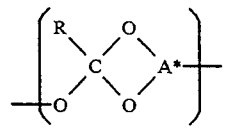

wherein R is hydrogen or $(C_1-C_{10})$alkyl and A* is

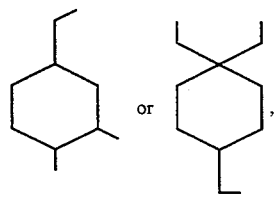

and mixtures thereof.

2. The polymer of claim 1, wherein R comprises hydrogen or $(C_1-C_6)$alkyl.

3. The polymer of claim 1, having a molecular weight of at least about 500 and up to about 50,000, as determined by gel permeation chromatography.

4. The polymer of claim 3, having a molecular weight of at least about 2000 and up to about 50,000, as determined by gel permeation chromatography.

5. The polymer of claim 1, comprising about 5 to 1000 mer units.

6. The polymer of claim 5, comprising up to about 150 mer units.

7. A bioerodible composition comprising the bioerodible polymer of claim 1 or mixtures thereof and an excipient.

8. The bioerodible composition of claim 7, wherein the excipient is selected from the group consisting of neutral, acidic and alkaline excipients.

9. The bioerodible composition of claim 8, further comprising an agent selected from the group consisting of colorants, diluents, odorants, skin permeation enhancers and stabilizers.

10. A controlled release composition, comprising a therapeutic agent dispersed in the bioerodible composition of claim 7.

11. The controlled release composition of claim 10 in unit form, wherein the therapeutic agent is present in an effective therapeutic amount.

12. The controlled release composition of claim 10, wherein the therapeutic agent comprises a wound or burn treating agent.

13. The controlled release composition of claim 10, wherein the therapeutic agent comprises a protein.

14. The controlled release composition of claim 10, wherein the therapeutic agent comprises an antiinfective agent.

15. The controlled release composition of claim 10, wherein the antiinfective agent comprises antibacterial or antiviral agents.

16. The controlled release composition of claim 10, wherein the therapeutic agent comprises an antiinflammatory agent.

17. The controlled release composition of claim 10, wherein the therapeutic agent comprises an antihypertensive agent.

18. The controlled release composition of claim 10, wherein the therapeutic agent comprises an adrenal corticosteriod.

19. The composition of claim 10, wherein the therapeutic agent comprises a periodontal disease treating agent.

20. The controlled release composition of claim 10, in solid implantable form.

21. The controlled release composition of claim 10, in flexible form.

22. The controlled release composition of claim 10, in a soft malleable dosage form.

23. The controlled release composition of claim 22, wherein the soft malleable dosage form is selected from the group consisting of ointments, creams and gels.

24. The controlled release composition of claim 10, in transdermal, transmucosal or intraocular form.

25. The controlled release composition of claim 10, wherein
the drug is present in an amount of about 0.001 to 79 wt %; and
the polymer is present in an amount of about 25 to 100 wt %.

26. A method for the controlled release of a therapeutic agent, comprising administering to a patient the controlled release bioerodible composition of claim 10.

27. A method of treating wounds or burns, comprising administering to a patient an effective amount of the controlled release bioerodible composition of claim 12.

28. A method for treating periodontal disease, comprising administering to an affected patient an effective amount of the controlled release bioerodible composition of claim 19.

29. A method of preparing a bioerodible polymer, comprising contacting a monomeric orthoester of the chemical formula

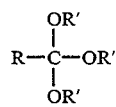

wherein R is hydrogen or $(C_1-C_{10})$alkyl and R' is lower alkyl, with a triol having the chemical formula

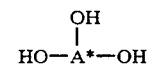

wherein A* is a mono- or dialkyleneclohexylene such that the triol has the structure

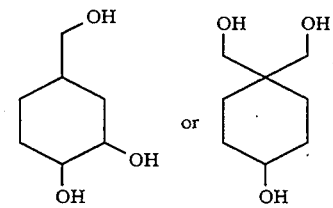

to form a bioerodible orthoester polymer comprising mer units of the chemical structure

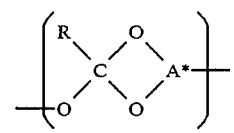

30. The method of claim 29, wherein R is hydrogen or lower alkyl.

31. The method of claim 30, wherein the number of mer units in the final polymer obtained is about 5 to 1000.

* * * * *